United States Patent [19]

Bundy

[11] 4,138,578

[45] Feb. 6, 1979

[54] 9-DEOXY-9-METHYLENE-16-PHENYL-17,18,19,20-TETRANOR-5,6,13,14-TETRADEHYDRO-4,4,5,5,13,14-HEXADEHYDRO-PGF$_1$ COMPOUNDS

[75] Inventor: Gordon L. Bundy, Portage, Mich.

[73] Assignee: The Upjohn Company, Kalamazoo, Mich.

[21] Appl. No.: 924,034

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ .......................................... C07C 177/00
[52] U.S. Cl. ................................... 560/55; 542/429; 562/465; 260/408; 260/410; 260/410.5; 260/410.9 R; 260/413

[58] Field of Search ..................... 560/55; 562/465; 260/408, 410, 410.5, 410.9 R, 413; 542/429

[56] References Cited

PUBLICATIONS

Derwent Abstract 61615x/33 BE839789 16.07.76.
Derwent Abstract 25533y/15 DT2642-558 07.04.77.

*Primary Examiner*—Paul J. Killos
*Attorney, Agent, or Firm*—Robert A. Armitage

[57] ABSTRACT

The present invention relates to novel 9-deoxy-9-methylene-16-phenyl-17,18,19,20-tetranor-5,6,13,14-tetradehydro-4,4,5,5,13,14-hexadehydro-PGF$_1$ compounds. These compounds are useful pharmacological agents, and are useful for the same purposes as the corresponding PGE-type compounds.

63 Claims, No Drawings

9-DEOXY-9-METHYLENE-16-PHENYL-17,18,19,20-TETRANOR-5,6,13,14-TETRADEHYDRO-4,4,5,5,13,14-HEXADEHYDRO-PGF$_1$ COMPOUNDS

CROSS REFERENCE TO RELATED APPLICATIONS

This application is a continuation-in-part of Ser. No. 786,249, filed Apr. 11, 1977, now issued as U.S. Pat. No. 4,118,584.

The present invention relates to novel 9-deoxy-9-methylene-16-phenyl-17,18,19,20-tetranor-5,6,13,14-tetradehydro-4,4,5,5,13,14-hexadehydro-PGF$_1$ compounds, the essential material constituting a disclosure of which is incorporated here by reference from U.S. Pat. No. 4,118,584.

I claim:

1. A prostaglandin analog of the formula

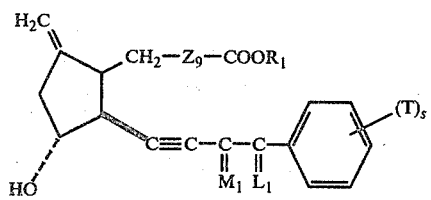

wherein M$_1$ is

or

wherein R$_5$ is hydrogen or methyl;
wherein L$_1$ is

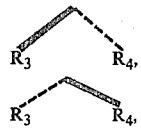

or a mixture of

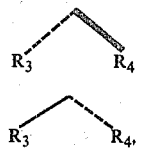

wherein R$_3$ and R$_4$ are hydrogen, mehtyl, or fluoro, being the same or different, with the proviso that one of R$_3$ and R$_4$ is fluoro only when the other is hydrogen or fluoro;
wherein Z$_9$ is —C≡C—CH$_2$—(CH$_2$)$_g$—CH$_2$ or —CH$_2$—C≡C—(CH$_2$)$_g$—CH$_2$—
wherein g is one, 2, or 3; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
Wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation, and the 1,11- or 1,15-lactones thereof.

2. A prostaglandin analog according to claim 1, wherein Z$_9$ is —CH$_2$—C≡C—(CH$_2$)$_g$—CH$_2$—.

3. A prostaglandin analog according to claim 2, wherein M$_1$ is

4. 9-Deoxy-9-methylene-15-epi-4,4,5,5-tetradehydro-16-phenyl-17,18,19,20-tetranor-13,14-didehydro-PGF$_1$, a prostaglandin analog according to claim 3.

5. A prostaglandin analog according to claim 2, wherein M$_1$ is

6. A prostaglandin analog according to claim 5, wherein s is zero or one and T is chloro, fluoro, or trifluoromethyl.

7. A prostaglandin analog according to claim 6, wherein g is 3.

8. 9-Deoxy-9-methylene-2a,2b-dihomo-15-methyl-4,4,5,5-tetradehydro-16-phenyl-17,18,19,20-tetranor-13,14-didehydro-PGF$_1$, a prostaglandin analog according to claim 7.

9. 9-Deoxy-9-methylene-2a,2b-dihomo-4,4,5,5-tetradehydro-16-phenyl-17,18,19,20-tetranor-13,14-didehydro-PGF$_1$, a prostaglandin analog according to claim 7.

10. A prostaglandin analog according to claim 6, wherein g is one.

11. A prostaglandin analog according to claim 10, wherein at least one of R$_3$ and R$_4$ is methyl.

12. A prostaglandin analog according to claim 11, wherein R$_3$ and R$_4$ are both methyl.

13. 9-Deoxy-9-methylene-16-methyl-4,4,5,5-tetradehydro-16-phenyl-18,19,20-trinor-13,14-didehydro-PGF$_1$, a prostaglandin analog according to claim 12.

14. A prostaglandin analog according to claim 10, wherein at least one of R$_3$ and R$_4$ is fluoro.

15. A prostaglandin analog according to claim 14, where R$_3$ and R$_4$ are both fluoro.

16. 9-Deoxy-9-methylene-16,16-difluoro-4,4,5,5-tetrahydro-16-phenyl-17,18,19,20-tetranor-13,14-didehydro-PGF$_1$, a prostaglandin analog according to claim 15.

17. A protaglandin analog according to claim 10, wherein R$_3$ and R$_4$ are both hydrogen.

18. A prostaglandin analog according to claim 17, wherein R$_5$ is methyl.

19. 9-Deoxy-9-methylene-15-methyl-4,4,5,5-tetradehydro-16-phenyl-17,18,19,20-tetranor-13,14-didehydro-PGF$_1$, a prostaglandin analog according to claim 18.

20. A prostaglandin analog according to claim 17, wherein R$_5$ is hydrogen.

21. 9-Deoxy-9-methylene-4,4,5,5-tetradehydro-16-phenyl-17,18,19,20-tetranor-13,14-didehydro-PGF$_1$, a prostaglandin analog according to claim 20.

22. A prostaglandin analog according to claim 1, wherein Z$_9$ is —C≡C—CH$_2$—(CH$_2$)$_g$—CH$_2$.

23. A prostaglandin analog according to claim 22, wherein $M_1$ is

24. A prostaglandin analog according to claim 23, wherein s is zero or one and T is chloro, fluoro, or trifluoromethyl.

25. A prostaglandin analog according to claim 24, wherein g is 3.

26. 9-Deoxy-9-methylene-2a,2b-dihomo-15-epi-15-methyl-16-phenyl-17,18,19,20-tetranor-5,6,13,14-tetradehydro-PGF$_2$, a prostaglandin analog according to claim 25.

27. 9-Deoxy-9-methylene-2a,2b-dihomo-15-epi-16-phenyl-17,18,19,20-tetranor-5,6,13,14-tetradehydro-PGF$_2$, a prostaglandin analog according to claim 25.

28. A prostaglandin analog according to claim 24, wherein g is one.

29. A prostaglandin analog according to claim 28, wherein at least one of $R_3$ and $R_4$ is methyl.

30. 9-Deoxy-9-methylene-15-epi-16-methyl-16-phenyl-18,19,20-trinor-5,6,13,14-tetradehydro-PGF$_2$, a prostaglandin analog according to claim 29.

31. A prostaglandin analog according to claim 28, wherein at least one of $R_3$ and $R_4$ is fluoro.

32. 9-Deoxy-9-methylene-15-epi-16,16-difluoro-16-phenyl-17,18,19,20-tetranor-5,6,13,14-tetradehydro-PGF$_2$, a prostaglandin analog according to claim 31.

33. A prostaglandin analog according to claim 28, wherein $R_3$ and $R_4$ are both hydrogen.

34. 9-Deoxy-9-methylene-15-epi-16-methyl-16-phenyl-17,18,19,20-tetranor-5,6,13,14-tetradehydro-PGF$_2$, a prostaglandin analog according to claim 33.

35. A prostaglandin analog according to claim 23, wherein $M_1$ is

36. A prostaglandin analog according to claim 35, wherein s is zero or one and T is chloro, fluoro, or trifluoromethyl.

37. A prostaglandin analog according to claim 36, whrein g is 3.

38. A prostaglandin analog according to claim 37, wherein at least one of $R_3$ and $R_4$ is methyl.

39. 9-Deoxy-9-methylene-2a,2b-dihomo-16-methyl-16-phenyl-18,19,20-trinor-5,6,13,14-tetradehydro-PGF$_2$, a prostaglandin analog according to claim 38.

40. A prostaglandin analog according to claim 37, wherein at least one of $R_3$ and $R_4$ is fluoro.

41. 9-Deoxy-9-methylene-2a,2b-dihomo-16,16-difluoro-16-phenyl-17,18,19,20-tetranor-5,6,13,14-tetradehydro-PGF$_2$, a prostaglandin analog according to claim 40.

42. A prostaglandin analog according to claim 37, wherein $R_3$ and $R_4$ are both hydrogen.

43. 9-Dexoy-9-methylene-2a,2b-dihomo-16-phenyl-17,18,19,20-tetranor-5,6,13,14-tetradehydro-PGF$_2$, a prostaglandin analog according to claim 42.

44. A prostaglandin analog according to claim 36, wherein g is one.

45. A prostaglandin analog according to claim 44, wherein at least one of $R_3$ and $R_4$ is methyl.

46. A prostaglandin analog according to claim 45, wherein $R_3$ and $R_4$ are both methyl.

47. 9-Deoxy-9-methylene-16-methyl-16-phenyl-18,19,20-trinor-5,6,13,14-tetradehydro-PGF$_2$, tris-(hydromethyl)aminomethane salt, a prostaglandin analog according to claim 46.

48. 9-Deoxy-9-methylene-16-methyl-16-phenyl-18,19,20-trinor-13,14-dihydro-5,6-didehydro-PGF$_2$, methyl ester, a prostaglandin analog according to claim 46.

49. 9-Deoxy-9-methylene-16-methyl-16-phenyl-18,19,20-trinor-5,6,13,14-tetradehydro-PGF$_2$, methyl ester, a prostaglandin analog according to claim 46.

50. A prostaglandin analog according to claim 44, wherein at least one of $R_3$ and $R_4$ is fluoro.

51. A prostaglandin analog according to claim 50, wherein $R_3$ and $R_4$ are both fluoro.

52. A prostaglandin analog according to claim 51, wherein $R_5$ is methyl.

53. 9-Deoxy-9-methylene-15-methyl-16,16-difluoro-16-phenyl-17,18,19,20-tetranor-5,6,13,14-tetradehydro-PGF$_2$, a prostaglandin analog according to claim 52.

54. A prostaglandin analog according to claim 51, wherein $R_5$ is hydrogen.

55. 9-Deoxy-9-methylene-16,16-difluoro-16-phenyl-17,18,19,20-tetranor-5,6,13,14-tetradehydro-PGF$_2$, a prostaglandin analog according to claim 54.

56. A prostaglandin analog according to claim 44, wherein $R_3$ and $R_4$ are both hydrogen.

57. A prostaglandin analog according to claim 56, wherein $R_5$ is methyl.

58. 9-Deoxy-9-methylene-15-methyl-16-phenyl-17,18,19,20-tetranor-5,6,13,14-tetradehydro-PGF$_2$, tris-(hydroxymethyl)aminomethane salt, a prostaglandin analog according to claim 57.

59. 9-Deoxy-9-methylene-15-methyl-16-phenyl-17,18,19,20-tetranor-5,6,13,14-tetradehydro-PGF$_2$, methyl ester, a prostaglandin analog according to claim 57.

60. 9-Deoxy-9-methylene-15-methyl-16-phenyl-17,18,19,20-tetranor-5,6,13,14-tetradehydro-PGF$_2$, a prostaglandin analog according to claim 57.

61. A prostaglandin analog according to claim 56, wherein $R_5$ is hydrogen.

62. 9-Deoxy-9-methylene-16-phenyl-17,18,19,20-tetranor-5,6,13,14-tetradehydro-PGF$_2$, methyl ester, a prostaglandin analog according to claim 61.

63. 9-Deoxy-9-methylene-16-phenyl-17,18,19,20-tetranor-5,6,13,14-tetradehydro-PGF$_2$, a prostaglandin according to claim 61.

* * * * *

UNITED STATES PATENT AND TRADEMARK OFFICE
CERTIFICATE OF CORRECTION

PATENT NO. : 4,138,578

DATED : February 6, 1979

INVENTOR(S) : Gordon L. Bundy

It is certified that error appears in the above-identified patent and that said Letters Patent are hereby corrected as shown below:

Column 3, line 35, "15-epi-16-methyl-" should read -- 15-epi- --;

Column 4, line 3, "9-Dexoy-" should read -- 9-Deoxy- --; line 17, "5,6-didehydro-$PGF_2$," should read -- 5,6-didehydro-5,6,13,14-tetradehydro-$PGF_2$, --; lines 21-22, "$PGF_2$, methyl ester," should read -- $PGF_2$, --.

Signed and Sealed this

*Seventh* Day of *August 1979*

[SEAL]

*Attest:*

LUTRELLE F. PARKER
*Attesting Officer*   *Acting Commissioner of Patents and Trademarks*